United States Patent [19]
Dussault et al.

[11] Patent Number: 6,130,093
[45] Date of Patent: Oct. 10, 2000

[54] WATER CONTAINER INSPECTION

[75] Inventors: Daniel Dussault, Amesbury; David H. Fine, Lincoln; David P. Rounbehler, North Chelmsford, all of Mass.

[73] Assignee: Thermedics Detection Inc., Chelmsford, Mass.

[21] Appl. No.: 08/972,451

[22] Filed: Nov. 18, 1997

Related U.S. Application Data

[60] Provisional application No. 60/031,120, Nov. 18, 1996.

[51] Int. Cl.$^7$ .................................................. G01N 35/02
[52] U.S. Cl. .............................. 436/47; 436/50; 436/172; 422/52; 422/65; 422/67; 422/83; 422/90; 422/91; 209/552; 209/576
[58] Field of Search ................................. 436/47, 48, 54, 436/106, 172, 50; 422/63, 65, 67, 83, 91, 52, 90; 73/23.35, 23.41; 209/576, 552

[56] References Cited

U.S. PATENT DOCUMENTS

| | | | |
|---|---|---|---|
| 4,221,961 | 9/1980 | Peyton | 250/223 B |
| 4,459,023 | 7/1984 | Reich et al. | 356/240 |
| 4,490,042 | 12/1984 | Wyatt | 356/340 |
| 4,551,627 | 11/1985 | Reich | 250/223 B |
| 4,830,192 | 5/1989 | Plester et al. | 209/523 |
| 4,858,767 | 8/1989 | Myers et al. | 209/3.1 |
| 4,858,768 | 8/1989 | Plester | 209/523 |
| 4,998,824 | 3/1991 | Littlejohn et al. | 250/226 |
| 5,002,397 | 3/1991 | Ingrum et al. | 250/226 |
| 5,067,616 | 11/1991 | Plester et al. | 209/523 |
| 5,086,483 | 2/1992 | Capps | 382/31 |
| 5,150,307 | 9/1992 | McCourt et al. | 250/223 R |
| 5,305,887 | 4/1994 | Krieg et al. | 209/3.1 |
| 5,318,911 | 6/1994 | Fine et al. | 436/47 |
| 5,350,565 | 9/1994 | Leveson et al. | 422/64 |
| 5,352,611 | 10/1994 | Fine et al. | 436/43 |
| 5,376,550 | 12/1994 | Fine et al. | 436/47 |
| 5,388,705 | 2/1995 | Fine et al. | |
| 5,397,540 | 3/1995 | Rounbehler et al. | 422/82.08 |
| 5,418,170 | 5/1995 | Rounbehler et al. | 436/111 |
| 5,435,198 | 7/1995 | Rounbehler et al. | 73/865.9 |
| 5,470,754 | 11/1995 | Rounbehler et al. | 436/106 |
| 5,472,882 | 12/1995 | Rounbehler et al. | 436/111 |
| 5,486,693 | 1/1996 | Achter et al. | 250/223 B |
| 5,510,620 | 4/1996 | Achter et al. | 250/339.12 |
| 5,523,565 | 6/1996 | Federer et al. | 250/281 |
| 5,528,036 | 6/1996 | Achter et al. | 250/339.12 |
| 5,536,935 | 7/1996 | Klotzsch et al. | |
| 5,558,836 | 9/1996 | Rounbehler et al. | |
| 5,561,068 | 10/1996 | Rounbehler et al. | 436/139 |
| 5,567,623 | 10/1996 | Rounbehler et al. | 436/158 |
| 5,569,606 | 10/1996 | Fine et al. | 436/43 |

FOREIGN PATENT DOCUMENTS

| | | |
|---|---|---|
| 0306307 | 8/1989 | European Pat. Off. . |
| WO 93/24841 | 12/1993 | WIPO . |
| WO 94/12860 | 6/1994 | WIPO . |

*Primary Examiner*—Long V. Le
*Attorney, Agent, or Firm*—Ernest V. Linek; Banner & Witcoff, Ltd.

[57] ABSTRACT

An apparatus is used to determine whether a container moving along a conveyor is suitable for storing water. The apparatus includes a sampler that obtains a sample from the interior of the container as the container moves along the conveyor. A PID is connected to the sampler to receive the sample and produce a signal corresponding to contents of the sample. A controller is connected to the PID and receives and analyzes the signal to determine whether the container is suitable for storing water. The apparatus may include a vacuum source connected to the PID that produces a reduced pressure for drawing the sample through the PID. A flow restrictor may be positioned between the sampler and PID. The flow restrictor may provide variable resistance to set a desired clearance time through the PID and sensitivity of the PID.

22 Claims, 4 Drawing Sheets

WATER CONTAINER INSPECTION

CROSS REFERENCE TO RELATED APPLICATION

This application claims priority from U.S. Provisional application Ser. No. 60/031,120, filed Nov. 18, 1996, which is incorporated by reference.

BACKGROUND

The popularity of refillable containers has increased as the costs, both social and financial, associated with disposal of packaging have become less acceptable. For example, in many countries, water and other beverages are sold in refillable bottles. These bottles are often made from a type of plastic known as polyethylene terephthalate.

After use, refillable containers are returned to a bottling plant where they are cleaned and inspected before being refilled. This inspection, in addition to checking for physical damage such as cracks, screens the containers to eliminate those that include contaminants that might degrade the flavor, safety, or other qualities of the product that they are to contain. The risk of contamination is greater when a container is made from plastic, as opposed to glass, because some contaminants can be absorbed into the plastic walls of the container. Absorbed contaminants can persist despite cleaning procedures, and can later leach into the product.

High speed chemical detection equipment for analyzing vapors given off by residues in containers to determine the chemical composition of the residues has become available at reasonable cost. This equipment, which enables detection of residues in a container without slowing down the container as the container moves along a conveyor line, has proven to be particularly useful in systems for removing from the conveyor line containers that have been identified as potentially being contaminated.

Chemical detection equipment has been applied in detecting contaminants in refillable, reusable plastic bottles as the bottles move along a high speed conveyor line so that contaminated bottles can be rejected from the conveyor line. An example of such equipment is set forth in U.S. Pat. No. 5,318,911, entitled "System for Sampling and Determining the Presence of Compounds in Containers", which is incorporated herein by reference. U.S. Pat. No. 5,318,911 discloses a sampling head with one tube blowing gas into the open top of a bottle and an adjacent tube sucking air from the interior of the bottle to obtain a sample. The sample is then analyzed using a chemiluminescence technique to detect contaminants as indicated, for example, by the presence of nitrogen compounds in the sample. Other techniques and issues related to detecting contaminants in moving containers are discussed in U.S. Pat. Nos. 5,569,606, entitled "Method and System for Sampling and Determining the Presence of Contaminants in Recyclable Plastic Materials"; 5,567,623, entitled "Method and System for Sampling and Determining the Presence of Compounds"; 5,561,068, entitled "Method and System for Sampling and Determining the Presence of Compounds"; 5,536,935, entitled "Detection of Foaming Contaminants in Containers Using Image Processing"; 5,528,036, entitled "Spectral Detection of Contaminants in Containers"; 5,510,620, entitled "Detection of Turbid or Foaming Contaminants in Containers"; 5,486,693, entitled "Detection of Turbid Contaminants in Containers by Detecting Scattered Radiant Energy"; 5,472,882, entitled "Method and System for Sampling and Determining the Presence of Salts of Ammonia and Amines in Containers"; 5,470,754, entitled "Method and System for Sampling and Determining the Presence of Compounds"; 5,435,198, entitled "System for Sampling and Determining the Presence of Salts of Ammonia and Amines in Containers"; 5,418,170, entitled "Method and System for Sampling and Determining the Presence of Salts of Ammonia and Amines in Containers"; 5,397,540, entitled "System for Injecting Fluid into Spaced Containers Moving at Variable Speeds"; 5,388,705, entitled "Rejector System for Conveyor Line"; 5,376,550, entitled "Method and System for Sampling and Determining the Presence of Compounds in Containers"; and 5,352,611, entitled "Method and System for Sampling and Determining the Presence of Compounds in Containers", all of which are incorporated by reference. Many of these techniques are implemented by the ALEXUS inspection system available from Thermedics Detection, Inc. of Chelmsford, Mass.

SUMMARY

The invention provides a technique for identifying containers suitable for use in storing water. The techniques described above have been successful in identifying and rejecting containers that are contaminated so as to be unsuitable for use in storing water or other beverages. However, the described techniques have been less successful in distinguishing containers suitable for storing water from other containers.

Many containers include residues of flavored beverages such as fruit juices, alcohol or soda. These containers are suitable for storing other flavored beverages because the amount of residue in the containers is insufficient to affect the flavor or other properties of the flavored beverage. However, these containers may be unsuitable for storing water because even a small amount of residue may affect the flavor of the water.

It has been found that a photo-ionization detector ("PID") may be used in conjunction with a primary detector, such as, for example, a chemiluminescence detector, to identify containers suitable for storing water. For example, the primary detector may be positioned along the conveyor line and configured to reject containers unsuitable for storing any beverages (e.g., containers contaminated with gasoline). The PID, which is positioned downstream of the primary detector, then monitors the containers that were not rejected by the primary detector to distinguish between containers suitable for storing water (e.g., new or uncontaminated containers) and containers suitable for storing flavored beverages (e.g., containers with residues of fruit juices or other flavored beverages). This arrangement works particularly well because, while the PID is extremely effective in distinguishing containers suitable for water from other suitable containers, the PID is less effective in detecting nitrogen-based contaminants that render containers unsuitable for reuse.

In some instances, the PID may be used without an associated primary detector. For example, the PID has been found to be effective in detecting contaminants commonly found in the large plastic water bottles used with many water coolers. As such, a system for inspecting these water bottles could include just the PID and would not need to include an additional detector.

In one general aspect, the invention provides a system for determining whether a container moving along a conveyor is suitable for storing water. The system includes a sampler configured to obtain a sample from the interior of the container as the container moves along the conveyor. A PID is connected to receive the sample from the sampler and is configured to produce a signal corresponding to contents of the sample. A controller is connected to receive the signal from the PID and is configured to analyze the signal to determine whether the container is suitable for storing water.

Embodiments may include one or more of the following features. For example, a vacuum source may be connected to the PID and configured to produce a reduced pressure for drawing the sample through the PID. A flow restrictor may be positioned between the sampler and the PID and may be configured to provide a variable flow resistance for use in setting a desired clearance time through the PID and a sensitivity of the PID. The system also may include an injector configured to inject a fluid into the container to ease collection of the sample by the sampler. The injector may be configured to heat the injected fluid before the fluid is injected into the container.

The controller may be configured to generate a rejection signal when the container is not suitable for storing water. A rejector connected to receive the rejection signal may be configured to remove the container from the conveyor in response to the rejection signal.

The system also may include a chemiluminescence detector connected to receive a sample from the interior of the container and to produce a signal corresponding to the contents of the sample. A second controller may be connected to the chemiluminescence detector to receive the signal from the detector and analyze the signal to determine whether the container is suitable for containing a beverage. The second controller may be configured to generate a rejection signal when the container is not suitable for containing a beverage. The system also may include a rejector to remove the container from the conveyor in response to the rejection signal.

The first controller may be configured to generate a water rejection signal when the container is unsuitable for containing water. The system may be configured with a separator to transfer the container to a beverage conveyor in response to the water rejection signal. The rejector may be located upstream of the separator. In this configuration, containers that are not suitable for storing beverages will be rejected by the rejector and containers that are not suitable for storing water will be separated from those that are by the separator. The first and second controllers may comprise a single unit.

In another general aspect, the invention features a system for determining whether a container moving along a container is contaminated. The system includes a sampler configured to obtain a sample from the interior of the container as the container moves along the conveyor, a PID connected to receive the sample from the sampler and to produce a signal corresponding to contents of the sample, a flow restrictor positioned between the sampler and PID, and a controller connected to receive the signal from the PID and configured to analyze the signal to determine whether the container is contaminated. A vacuum source is connected to the PID and configured to produce a reduced pressure for drawing the sample through the PID.

The flow restrictor may be configured to provide a variable flow resistance for use in setting a desired clearance time through the PID and a sensitivity for the PID. An injector may be configured to inject a fluid into the container to ease collection of the sample by the sampler.

Other features and advantages will be apparent from the following detailed description, including the drawings, and from the claims.

DETAILED DESCRIPTION

Figure 1:
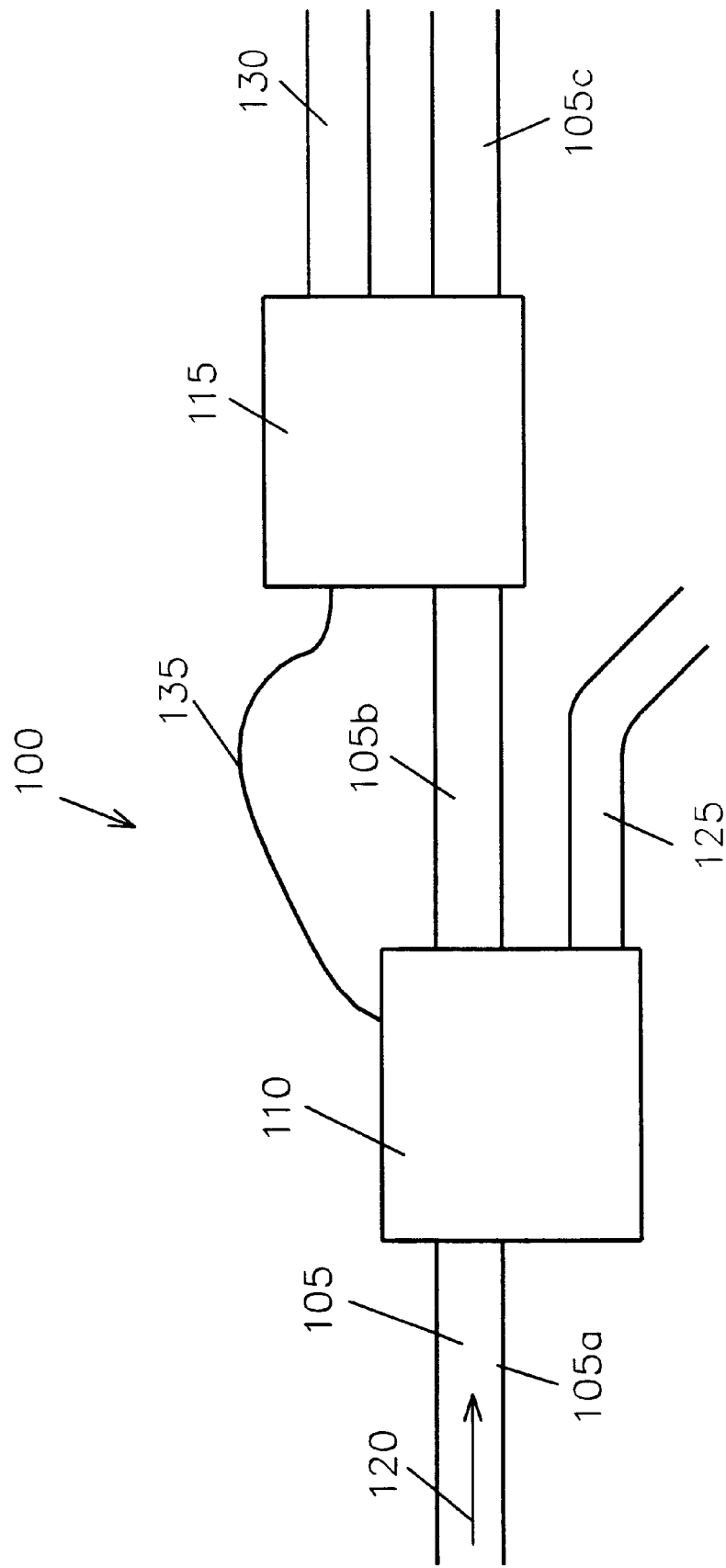
FIG. 1 is a block diagram of a bottle inspection system.

Referring to FIG. 1, a bottle inspection system 100 includes a conveyor line 105 along which is positioned a primary inspection station 110 and a secondary inspection station 115. Bottles move along the conveyor line 105 in the direction indicated by the arrow 120.

Bottles moving along a first section 105a of the conveyor line 105 may include new bottles, bottles that were filled previously with water or are otherwise uncontaminated, bottles that were filled previously with flavored beverages, bottles that are contaminated with materials such as detergent or gasoline, and bottles that include foreign objects. These bottles enter the primary inspection station 110, which may be for example, an ALEXUS inspection system as noted above. The inspection station 110 detects contaminated bottles or bottles that include foreign objects and rejects those bottles onto a secondary conveyor line 125. Accordingly, a second section 105b of the conveyor line may include new bottles, bottles that were filled previously with water or are otherwise uncontaminated, and bottles that were filled previously with flavored beverages.

Bottles travelling along the conveyor section 105b enter the secondary inspection station 115. The inspection station 115, which includes a PID, detects bottles that were filled previously with flavored beverages and rejects those bottles onto a secondary conveyor line 130. The conveyor line 130 then conveys the rejected bottles to a bottling line that bottles flavored beverages.

After the flavored-beverage bottles are rejected by the inspection station 115, a third section 105c of the conveyor line may include new bottles and bottles that were filled previously with water or are otherwise uncontaminated. The conveyor line 105 then conveys these bottles to a bottling line that bottles water. Bottles that were filled previously with flavored beverages are not used in bottling water because residues of the flavored beverages may affect the flavor of the water.

Figure 2:
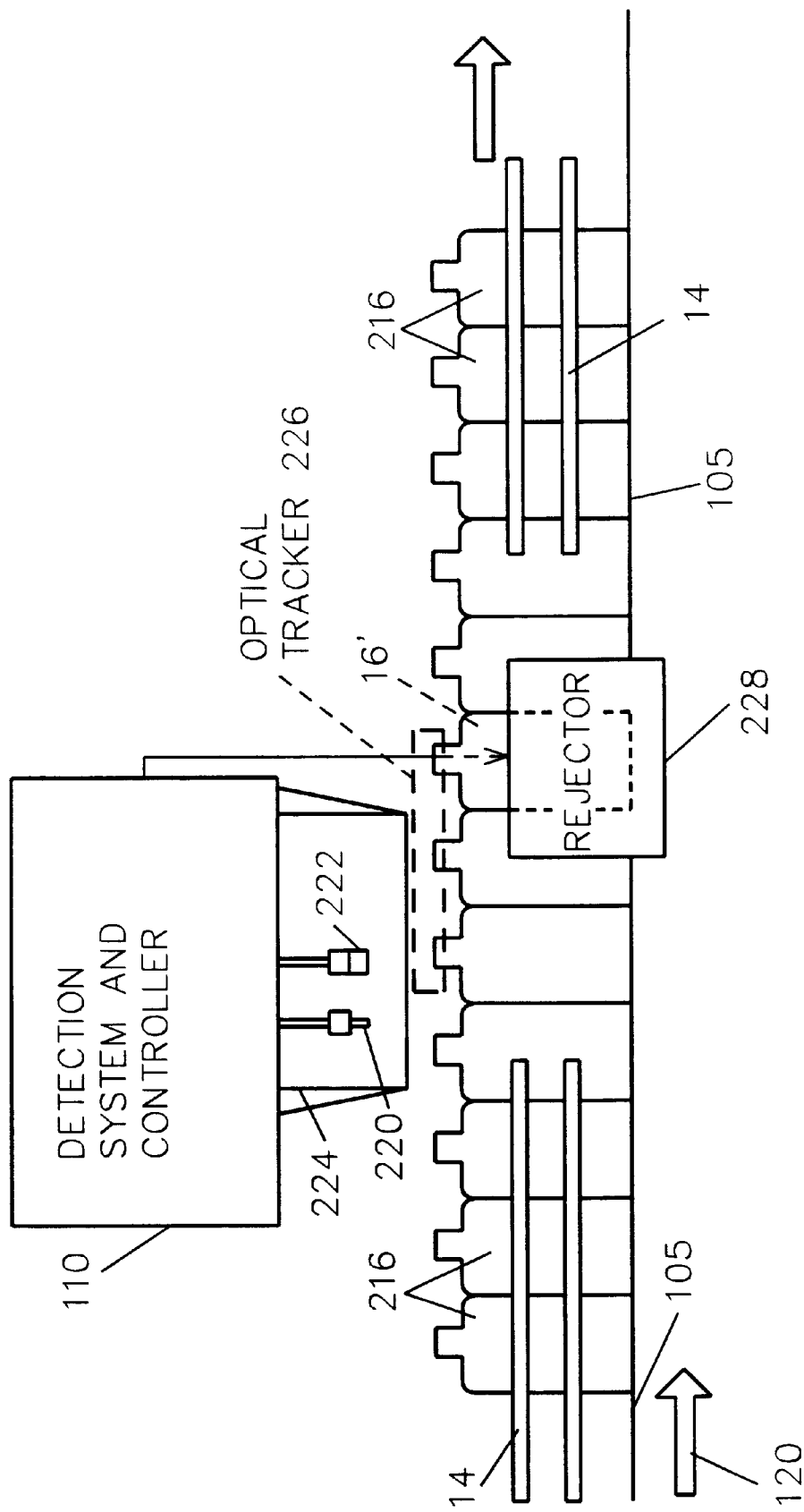
FIGS. 2 and 3 are block diagrams of a primary inspection station of the system of FIG. 1.
Figure 3:
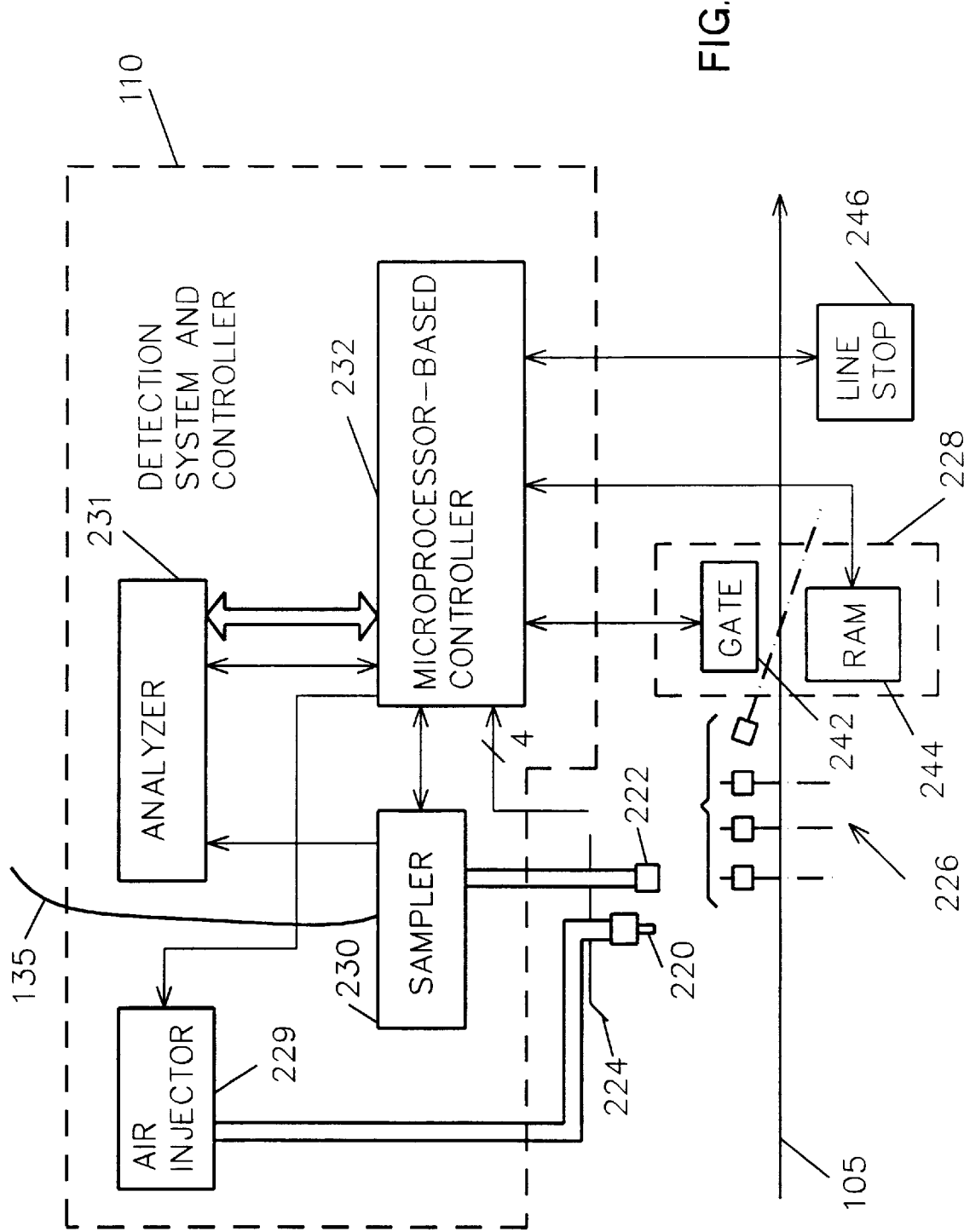

As shown in FIGS. 2 and 3, the primary inspection station 110 is equipped with an injection nozzle 220 and a sample inlet 222 mounted in juxtaposition under a hood 224 directly above a line of bottles 216. The injection nozzle 220 is aimed to inject a fluid into the open tops of bottles 216 as they pass beneath the nozzle. The bottles 216 are tracked by an optical tracking system 226 that extends from the sample inlet 222 to a rejector station 228 where a contaminated bottle 216' discovered by the inspection station 110 is knocked off of the line 105 and onto the line 125.

Referring more particularly to FIG. 3, an injector 229 injects pulses of heated or unheated air or an inert gas into the open top of a bottle as the bottle passes beneath the injector nozzle 220. A sample cloud is released above the bottle, and an air sample from the cloud is withdrawn through sample inlet 222 by an evacuator sampler 230. A portion of the withdrawn sample is passed from the sampler to a residue analyzer 231. The remainder of the evacuated sample is vented, passed back to the air injector 229 or passed to the secondary inspection station 115 through a heated transfer line 135. The analyzer 231 conducts an analysis of the sample for the presence of contaminants, indicated for example by nitrogen compounds in the sample cloud, by means of a chemiluminescence technique. The analyzer 231 issues a signal indicating the magnitude of any detected contaminant to a microprocessor-based controller 232.

Controller 232 is a programmable computer configured and equipped with input and output features to operate the detector and rejection systems. Controller 232 issues commands to the various components based on programmed timing and inputs from optical tracker system 226 as well as from the analyzer 231.

Figure 4:
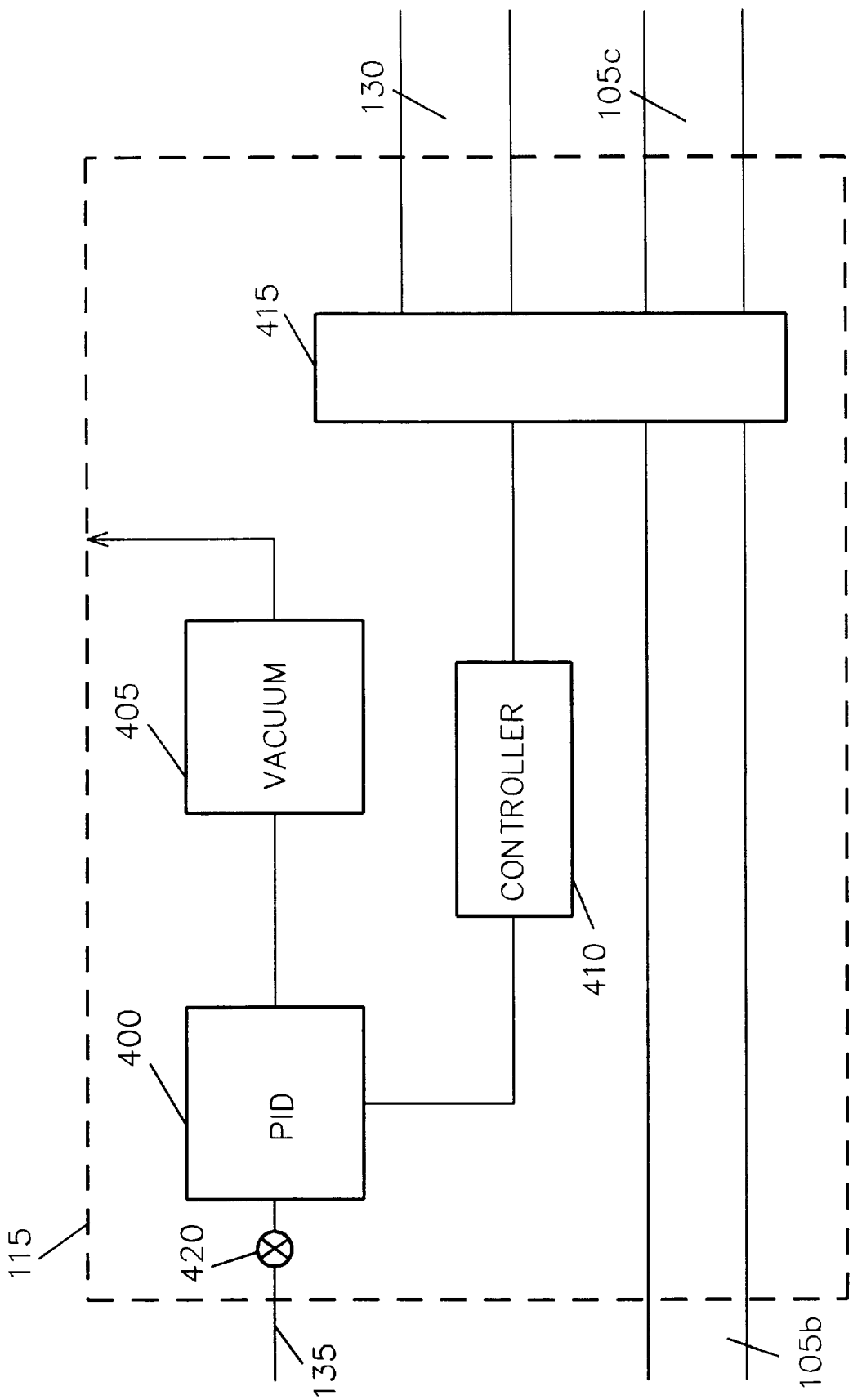
FIG. 4 is a block diagram of a secondary inspection station of the system of FIG. 1.

As shown in FIG. 4, the sample is drawn through the heated transfer line 135 and into a heated PID 400 by a vacuum source 405. Thereafter, the sample is vented to atmosphere.

The PID 400 may be, for example, an OVM-580 PID available from Thermal Environmental Instruments of Franklin, Mass. The PID ionizes the sample by passing the sample past an ultra-violet lamp. Electrically-charged particles produced during the ionization strike a collector and form an electric current in the ionization chamber that is proportional to the concentration of contaminants present in the sample stream. The PID 400 detects residues of flavored beverages by detecting, for example, hydrocarbons included in citrus flavors and alcohol.

The signal from the PID 400 is passed to a controller 410 that analyzes the signal. When the signal exceeds a threshold level, which indicates that the corresponding bottle contains residues of flavored beverages, the controller 410 signals a separator/rejector 415 to transfer the bottle to the conveyor line 130.

In some implementations, the transfer line 135 may be eliminated and a sampling apparatus may be included in the secondary inspection station 115. As previously noted, other implementations may eliminate the primary inspection station 110 altogether and include just the inspection station 115.

The clearance time of the PID (i.e., the time required to clear the residue of a sample from the PID chamber) is critical to the speed at which the conveyor can operate with a given number of PIDs. A decrease in clearance time increases the rate at which bottles can be sampled, since the residue of a sample must be removed from the chamber so that it does not affect the next sample ionized in the PID. To decrease the clearance time, vacuum source 405 pulls the sample through PID 400. As the vacuum exerted by vacuum source 405 increases, the clearance time decreases. However, increasing the vacuum requires considerable energy.

To decrease the clearance time without substantially increasing the energy required, a restrictor 420 is placed in line 135 between PID 400 and primary inspection station 110. The degree of closure of restrictor 420 can be varied to increase the resistance in line 135 until the clearance time and energy use are at desired levels.

An additional benefit of reducing the clearance time while ionizing the same quantity of a sample is that the sensitivity of the PID is increased. In one implementation, the clearance time is in the range of 200 to 350 milliseconds.

The position of the restrictor affects the clearance time. For instance, if the restrictor is placed between the vacuum source and the PID, the pressure in the chamber is close to atmospheric and a sample in the PID chamber flows through the chamber at a relatively low velocity. If the restrictor is placed in the line before the PID chamber, the pressure in the chamber is close to the vacuum pressure and the sample flows through the chamber at a relatively high velocity. Consequently, with a vacuum applied to the PID chamber, the sample will pass more rapidly through the chamber and the PID will be able to analyze the sample more rapidly than if the pressure in the chamber were near atmospheric pressure.

Other embodiments are within the scope of the following claims.

What is claimed is:

1. An apparatus for determining whether a container moving along a conveyor is suitable for storing water, the apparatus comprising:
    a sampler configured to obtain a sample from an interior of the container as the container moves along the conveyor;
    a PID connected to receive the sample from the sampler and configured to produce a signal reflecting the presence or the absence of flavored beverage residue in the sample; and
    a controller connected to receive the signal from the PID and configured to analyze the signal to determine whether the container is suitable for storing water.

2. The apparatus of claim 1, further comprising a vacuum source connected to the PID and configured to produce a reduced pressure for drawing the sample through the PID.

3. The apparatus of claim 2, further comprising a flow resistor positioned between the sampler and the PID.

4. The apparatus of claim 3, wherein the flow restrictor is configured to provide a variable flow resistance for use in setting a desired clearance time through the PID and sensitivity of the PID.

5. The apparatus of claim 1, further comprising an injector configured to inject a fluid into the container to ease collection of the sample by the sampler.

6. The apparatus of claim 5, wherein the injector is configured to heat the injected fluid before the fluid is injected into the container.

7. The apparatus of claim 1, wherein the controller is configured to generate a rejection signal when the container is not suitable for storing water, the apparatus further comprising a rejector connected to receive the rejection signal and configured to remove the container from the conveyor in response to the rejection signal.

8. The apparatus of claim 1, further comprising:
    a chemiluminescence detector connected to receive a sample from the interior of the container and to produce a signal corresponding to contents of the sample; and
    a second controller connected to receive the signal from the chemiluminescence detector and configured to analyze the signal to determine whether the container is suitable for storing a beverage.

9. The apparatus of claim 8, wherein the second controller is configured to generate a rejection signal when the container is not suitable for storing a beverage, the apparatus further comprising a rejector configured to remove the container from the conveyor in response to the rejection signal.

10. The apparatus of claim 9, wherein the first controller is configured to generate a water rejection signal when the container is not suitable for containing water, the apparatus further comprising a separator configured to transfer the container to a beverage conveyor in response to the water rejection signal.

11. The apparatus of claim 10, wherein the rejector is located upstream of the separator.

12. The apparatus of claim 8, wherein the first and second controllers comprise a single unit.

13. An apparatus for determining whether a container moving along a conveyor is contaminated, the apparatus comprising:
- a sampler configured to obtain a sample from the interior of the container as the container moves along the conveyor;
- a PID connected to receive the sample from the sampler and to produce a signal reflecting the presence or the absence of flavored beverage residue in the sample;
- a flow restrictor positioned between the sampler and the PID; and
- a controller connected to receive the signal to determine whether the container is suitable for storing water.

14. The apparatus of claim 13, further comprising a vacuum source connected to the PID and configured to produce a reduced pressure for drawing the sample through the PID.

15. The apparatus of claim 14, wherein the flow restrictor is configured to provide a variable flow resistance for use in setting a desired clearance time through the PID and the sensitivity of the PID.

16. The apparatus of claim 15, further comprising an injector configured to inject a fluid into the container to ease collection of the sample by the sampler.

17. A method for determining whether a container moving along a conveyor is suitable for storing water, the method comprising:
- obtaining a sample from the interior of a container as the container moves along a conveyor;
- passing the sample through a PID to produce a signal reflecting the presence or the absence of flavored beverage residue in the sample; and
- analyzing the signal to determine whether the container is suitable for storing water.

18. The method of claim 17, further comprising applying a reduced pressure to the PID to draw the sample through the PID.

19. The method of claim 18, further comprising restricting flow of the sample into the PID.

20. The method of claim 17, further comprising injecting a fluid into the container to ease collection of the sample by the sampler.

21. The method of claim 20, further comprising heating the fluid before injecting the fluid into the container.

22. The method of claim 21, further comprising, upon determining that the container is unsuitable for storing water, removing the container from the conveyor.

* * * * *